(12) United States Patent
Petcavich

(10) Patent No.: US 10,625,234 B2
(45) Date of Patent: Apr. 21, 2020

(54) METHOD OF FABRICATING CELL ARRAYS AND USES THEREOF

(71) Applicant: StemoniX Inc., Eden Prairie, MN (US)

(72) Inventor: Robert John Petcavich, The Woodlands, TX (US)

(73) Assignee: StemoniX Inc., Eden Prairie, MN (US)

( * ) Notice: Subject to any disclaimer, the term of this patent is extended or adjusted under 35 U.S.C. 154(b) by 133 days.

(21) Appl. No.: 14/839,170

(22) Filed: Aug. 28, 2015

(65) Prior Publication Data

US 2016/0059203 A1 Mar. 3, 2016

Related U.S. Application Data

(60) Provisional application No. 62/070,508, filed on Aug. 28, 2014.

(51) Int. Cl.
*B01J 19/00* (2006.01)

(52) U.S. Cl.
CPC .. *B01J 19/0046* (2013.01); *B01J 2219/00362* (2013.01); *B01J 2219/00531* (2013.01); *B01J 2219/00639* (2013.01); *B01J 2219/00711* (2013.01); *B01J 2219/00743* (2013.01)

(58) Field of Classification Search
None
See application file for complete search history.

(56) References Cited

U.S. PATENT DOCUMENTS

| | | | |
|---|---|---|---|
| 5,981,268 | A | 11/1999 | Kovacs et al. |
| 6,565,813 | B1 | 5/2003 | Garyantes |
| 2002/0049160 | A1 | 4/2002 | Huang et al. |
| 2005/0169962 | A1 | 8/2005 | Bhatia et al. |
| 2007/0017530 | A1 | 1/2007 | Syed et al. |
| 2007/0122392 | A1 | 5/2007 | Gerecht-nir et al. |
| 2007/0280987 | A1 | 12/2007 | Helmus et al. |
| 2008/0193536 | A1 | 8/2008 | Khademhosseini et al. |
| 2010/0055733 | A1 | 3/2010 | Lutolf et al. |
| 2010/0120626 | A1 | 5/2010 | Ross et al. |
| 2010/0317103 | A1 | 12/2010 | Cho et al. |
| 2011/0306041 | A1 | 12/2011 | Viovy et al. |
| 2012/0053084 | A1 | 3/2012 | Gerber et al. |
| 2012/0149781 | A1 | 6/2012 | Lee et al. |
| 2012/0308531 | A1 | 12/2012 | Pinxteren et al. |
| 2013/0029421 | A1 | 1/2013 | Komvopoulos et al. |
| 2013/0034904 | A1 | 2/2013 | Fan et al. |
| 2013/0171116 | A1 | 7/2013 | Shoham et al. |
| 2013/0203086 | A1 | 8/2013 | Achyuta et al. |
| 2013/0217113 | A1 | 8/2013 | Srinivasan et al. |
| 2014/0142370 | A1 | 5/2014 | Wong et al. |
| 2014/0287506 | A1 | 9/2014 | Sanyal et al. |
| 2016/0059203 | A1 * | 3/2016 | Petcavich ............ B01J 19/0046 506/26 |
| 2017/0002324 | A1 | 1/2017 | Petcavich |
| 2017/0107488 | A1 | 4/2017 | Petcavich |
| 2017/0166857 | A1 | 6/2017 | Petcavich |
| 2018/0113118 | A1 | 4/2018 | Petcavich |
| 2018/0291336 | A1 | 10/2018 | Petcavich |
| 2019/0161717 | A1 | 5/2019 | Petcavich |
| 2019/0177691 | A1 | 6/2019 | Petcavich |

FOREIGN PATENT DOCUMENTS

| | | |
|---|---|---|
| CN | 102156158 A | 8/2011 |
| DE | 102014003465 A1 | 9/2015 |
| JP | 2003503715 A | 1/2003 |
| JP | 2005505747 A | 2/2005 |
| JP | 2007516699 A | 6/2007 |
| JP | 2008199962 A | 9/2008 |
| JP | 2013135685 A | 7/2013 |
| JP | 2014519825 A | 8/2014 |
| JP | 2017532061 A | 11/2017 |
| JP | 2018536424 A | 12/2018 |
| JP | 2018537073 A | 12/2018 |
| SG | 2011088213 | 7/2011 |
| SG | 2014063194 | 5/2014 |
| WO | WO-2011/088213 A1 | 7/2011 |
| WO | WO-2012168295 A1 | 12/2012 |
| WO | WO-2014063194 A1 | 5/2014 |
| WO | WO-2014110559 A1 | 7/2014 |
| WO | WO-2014144219 A1 | 9/2014 |
| WO | WO-2014145975 A2 | 9/2014 |
| WO | WO-2015/069943 A1 | 5/2015 |
| WO | WO-2016033501 A1 | 3/2016 |
| WO | WO-2016090486 A1 | 6/2016 |
| WO | WO-2017066663 A1 | 4/2017 |
| WO | WO-2017100705 A1 | 6/2017 |
| WO | WO-2018026925 A1 | 2/2018 |
| WO | WO-2018026929 A1 | 2/2018 |
| WO | WO-2018075890 A1 | 4/2018 |

OTHER PUBLICATIONS

Nichol, et al. (2010) "Cell-laden microengineered gelatin methacrylate hydrogels", Biomaterials, 31(21): 5536-44.*
Wong, et al. (2009) "Advancing Microarray Assembly with Acoustic Dispensing Technology", Analytical Chemistry, 81(1): 509-14.*
Geyer, et al. (2011) "Superhydrophobic-Superhydrophilic Micropatterning: Towards Genome on a Chip Cell Microarrays", Angewandte Chemie, 50: 8424-27.*
Fernandes, et al. (2009) "High-throughput cellular microarray platforms: applications in drug discovery, toxicology and stem cell research", Trends in Biotechnology, 27(6): 342-49.*
Mordwinkin, et al. (2013) "A Review of Human Pluripotent Stem Cell-Derived Cardiomyocytes for High-Throughput Drug Discovery, Cardiotoxicity Screening and Publication Standards", Journal of Cardiovascular Translational Research, 6(1): 22-30.*
Braam, et al. (2010) "Inhibition of Rock improves survival of human embryonic stem cell-derived cardiomyocytes after dissociation", Annals of the New York Academy of Science, 1188: 52-57. (Year: 2010).*

(Continued)

*Primary Examiner* — Robert M Kelly

(74) *Attorney, Agent, or Firm* — Schwegman Lundberg & Woessner, P.A.

(57) ABSTRACT

The present disclosure provides a fabrication process that results in creating large arrays of living cells, such as stem cells, which are subsequently exposed to nanoliter quantities of compounds to test the efficacy on cellular metabolism.

19 Claims, 1 Drawing Sheet

(56) References Cited

OTHER PUBLICATIONS

"International Application Serial No. PCT/US15/47494, International Search Report dated Nov. 6, 2015", 4 pgs.
"International Application Serial No. PCT/US15/47494, Written Opinion dated Nov. 6, 2015", 6 pgs.
"International Application Serial No. PCT/US2015/047494, International Preliminary Report on Patentability dated Mar. 9, 2017", 8 pgs.
Ali, Khademhosseini, et al., "Micromolding of photoelectrically hyaluronic acid for cell encapsulation and entrapment", Journal of Biomedical Materials Research Part A vol. 79A, No. 3, (Jan. 1, 2006), 522-532.
Alireza, Dolatshahi Pirouz, et al., "A combinatorial cell-laden gel microarray for inducing osteogenic differentiation of human mesenchymal stem cells", Scientific Reports, vol. 4, (Jan. 29, 2014), 2 pgs.
"European Application Serial No. 15762878.5, Response filed Oct. 16, 2017 to Communication pursuant to Rules 161(1) and 162 EPC dated Apr. 4, 2017", 9 pgs.
"Singaporean Application Serial No. 11201701540P, Response filed Aug. 24, 2017 to Request Combined Search and Examination dated Feb. 27, 2017", 9 pgs.
"European Application Serial No. 15762878.5, Communication Pursuant to Article 94(3) EPC dated Jan. 4, 2018", 5 pgs.
"Singaporean Application Serial No. 11201701540P, Written Opinion dated Dec. 28, 2017", 7 pgs.
Dolatshahi-Pirouz, Alireza, et al., "A combinatorial cell-laden gel microarray for inducing osteogenic differentiation of human mesenchymal stem cells", Scientific Reports, (Jan. 29, 2014), 1-9.
Nichol, Jason W., et al., "Cell-laden microengineered gelatin methacrylate hydrogels", National Institutes of Health, (Jul. 31, 2010), 1-20.
Peppas, Nicholas A., et al., "Hydrogels in Biology and Medicine: From Molecular Principles of Bionanotechnology", Advanced Materials, (2006), 1345-1360.
"European Application Serial No. 15762878.5, Response filed Jul. 16, 2018 to Communication Pursuant to Article 94(3) EPC dated Jan. 4, 2018", 34 pgs.
"Japanese Application Serial No. 2017-530976, Office Action dated Jul. 3, 2018", w/ English translation, 7 pgs.
"European Application Serial No. 157628785, Communication Pursuant to Article 94(3) EPC dated Nov. 20, 2018", 4 pgs.
"Japanese Application Serial No. 2017-530976, Response filed Oct. 3, 2018 to Office Action dated Jul. 3, 2018", w English Claims, 12 pgs.
"Singaporean Application Serial No. 11201701540P, Written Opinion dated Nov. 7, 2018", 6 pgs.
"U.S. Appl. No. 15/199,419, Advisory Action dated Jul. 20, 2018", 5 pgs.
"U.S. Appl. No. 15/199,419, Final Office Action dated Apr. 16, 2018", 19 pgs.
"U.S. Appl. No. 15/199,419, Final Office Action dated May 30, 2018", 25 pgs.
"U.S. Appl. No. 15/199,419, Non Final Office Action dated Jan. 25, 2019", 25 pgs.
"U.S. Appl. No. 15/199,419, Non Final Office Action dated Nov. 8, 2017", 21 pgs.
"U.S. Appl. No. 15/199,419, Response filed Nov. 8, 2017 to Non Final Office Action dated Nov. 8, 2017", 14 pgs.
"U.S. Appl. No. 15/199,419, Response filed Aug. 16, 2018 to Final Office Action dated apr. 16, 2018", 8 pgs.
"U.S. Appl. No. 15/199,419, Response filed Aug. 29, 2017 to Restriction Requirement dated Jun. 23, 2017", 6 pgs.
"U.S. Appl. No. 15/199,419, Response filed Apr. 23, 2019 to Non Final Office Action dated Jan. 25, 2019", 10 pgs.
"U.S. Appl. No. 15/199,419, Response filed Jun. 19, 2018 to Final Office Action dated Apr. 16, 2018", 9 pgs.
"U.S. Appl. No. 15/199,419, Response filed Aug. 29, 2019 to Final Office Action dated May 31, 2019", 9 pgs.
"U.S. Appl. No. 15/199,419, Restriction Requirement dated Jun. 23, 2017", 10 pgs.
"U.S. Appl. No. 15/293,563, Advisory Action dated Jun. 19, 2019", 5 pgs.
"U.S. Appl. No. 15/293,563, Final Office Action dated Apr. 3, 2019", 11 pgs.
"U.S. Appl. No. 15/293,563, Non Final Office Action dated Aug. 29, 2019", 13 pgs.
"U.S. Appl. No. 15/293,563, Non Final Office Action dated Nov. 29, 2018", 11 pgs.
"U.S. Appl. No. 15/293,563, Response filed Feb. 26, 2019 to Non Final Office Action dated Nov. 29, 2018", 6 pgs.
"U.S. Appl. No. 15/293,563, Response filed Sep. 12, 2018 to Restriction Requirement dated Jul. 16, 2018", 5 pgs.
"U.S. Appl. No. 15/293,563, Response filed Jun. 3, 2019 to Final Office Action dated Apr. 3, 2019", 6 pgs.
"U.S. Appl. No. 15/293,563, Response filed Aug. 5, 2019 to Advisory Action dated Jun. 19, 2019", 6 pgs.
"U.S. Appl. No. 15/293,563, Restriction Requirement dated Jul. 16, 2018", 6 pgs.
"U.S. Appl. No. 15/374,961, Final Office Action dated Jun. 13, 2019", 17 pgs.
"U.S. Appl. No. 15/374,961, Non Final Office Action dated Nov. 11, 2018", 15 pgs.
"U.S. Appl. No. 15/374,961, Response filed Feb. 28, 2019 to Non Final Office Action dated Nov. 30, 2018", 7 pgs.
"U.S. Appl. No. 15/374,961, Response filed Oct. 2, 2018 to Restriction Requirement dated Aug. 2, 2018", 6 pgs.
"U.S. Appl. No. 15/374,961, Restriction Requirement dated Aug. 2, 2018", 7 pgs.
"U.S. Appl. No. 15/789,335, Non Final Office Action dated Jul. 26, 2019", 21 pgs.
"U.S. Appl. No. 15/789,335, Response filed Apr. 8, 2019 to Restriction Requirement dated Feb. 7, 2019", 5 pgs.
"U.S. Appl. No. 15/789,335, Restriction Requirement dated Feb. 7, 2019", 8 pgs.
"European Application Serial No. 16829018.7, Communication Pursuant to Article 94(3) EPC dated May 28, 2019", 6 pgs.
"European Application Serial No. 16829018.7, Response filed Feb. 5, 2019 to Communication Pursuant to Rules 161(1) and 162 EPC dated Jul. 26, 2019", 8 pgs.
"International Application Serial No. PCT/US2016/057172, International Preliminary Report on Patentability dated Apr. 26, 2018", 7 pgs.
"International Application Serial No. PCT/US2016/057172, International Search Report dated Jan. 17, 2017", 5 pgs.
"International Application Serial No. PCT/US2016/057172, International Written Opinion dated Jan. 17, 2017", 5 pgs.
"International Application Serial No. PCT/US2016/066014, International Preliminary Report on Patentability dated Jun. 21, 2018", 8 pgs.
"International Application Serial No. PCT/US2016/066014, International Search Report dated Apr. 5, 2017", 5 pgs.
"International Application Serial No. PCT/US2016/066014, Written Opinion dated Apr. 5, 2017", 9 pgs.
"International Application Serial No. PCT/US2017/045114, International Preliminary Report on Patentability dated Feb. 14, 2019", 9 pgs.
"International Application Serial No. PCT/US2017/045114, International Search Report dated Oct. 23, 2017", 5 pgs.
"International Application Serial No. PCT/US2017/045114, Written Opinion dated Oct. 23, 2017", 7 pgs.
"International Application Serial No. PCT/US2017/045119, International Preliminary Report on Patentability dated Feb. 14, 2019", 8 pgs.
"International Application Serial No. PCT/US2017/045119, International Search Report dated Oct. 27, 2017", 3 pgs.
"International Application Serial No. PCT/US2017/045119, Written Opinion dated Oct. 27, 2017", 6 pgs.
"International Application Serial No. PCT/US2017/057591, International Search Report dated Jan. 30, 2018", 6 pgs.
"International Application Serial No. PCT/US2017/057591, Written Opinion dated Jan. 30, 2018", 5 pgs.

(56) References Cited

OTHER PUBLICATIONS

"Japanese Application Serial No. 2018-519441, Notification of Reasons for Refusal dated May 15, 2019", W/ English Translation, 5 pgs.

"Japanese Application Serial No. 2018-519441, Response Filed Aug. 14, 2019 to Notification of Reasons for Refusal dated May 14, 2019", w/English Claims, 9 pgs.

"Japanese Application Serial No. 2018-530058, Notification of Reasons for Refusal dated Jul. 9, 2019", w/ English translation, 12 pgs.

"Modeling pain with rat dorsal root ganglion neurons on MEAs", Axion Biosystems, [Online] Retrieved from the Internet: <https://www.axionbiosystems.com/sites/default/files/resources/modeling_pain_with_rat_dorsaLroot_ganglion_neurons_on_meas.pdf>, (2014), 8 pgs.

Amin, Hayder, et al., "Electrical Responses and Spontaneous Activity of Human iPS-Derived Neuronal Networks Characterized for 3-month Culture with 4096-Electrode Arrays", Frontiers in Neuroscience, vol. 10, Article 121, (Mar. 30, 2016), 1-15.

Anke, Tukker M, "Is the time right for in vitro neurotoxicity testing using human iPSC-derived neurons?", Alternatives to Animal Experimentation: Altex 33 (3), (2016), 261-271.

BLAU, Axel, "Cell adhesion promotion strategies for signal transduction", Current Opinion in Colloid and Interface Science 18, (2013), 12 pages.

Booth, Ross, et al., "Characterization of microfluidic in vitro model of the blood-brain barrier", Lab on Chip Royal Society of Chemistry vol. 12, No. 10, (Jan. 1, 2012), 17841792.

Brown, Jacquelyn A, et al., "Recreating blood-brain barrier physiology and structure on chip novel neurovascular microfluidic bioreactor", Biomicrofluidics 9, (2015), 16 pgs.

Chen, Jun, et al., "Chapter 18: In vitro and in vivo assays for the discovery of analgesic drugs targetting TRP channels", TRP Channels, [Online] Retrieved from the Internet: <https://www.ncbi.nlm.nih.gov/books/NBK92815/>, (2011), 17 pgs.

Claverol Tinture, E, et al., "Communication; Multielectrode arrays with elastomeric microstructured oberlays for extracellular recordings from patterned neurons; Communication", Journal of Neural Engineering, vol. 2, No. 2, (Jun. 1, 2005), pp. L1-L7.

Claverol-Tinture, E, et al., "Multi electrode arrays with elastomeric microstructured overlays for extracellular recordings from patterned neurons", Communication; Journal of Neural Engineering, Institute of Physics Publishing, Bristol, GB, vol. 2, No. 2, (Jun. 1, 2005), L1-L7.

Cucullo, Luca, et al., "Development of a Humanized in Vitro Blood?Brain Barrier Model to Screen for Brain Penetration of Antiepileptic Drugs", Epilepsia, vol. 48, No. 3, (2007), 505-516.

Cwikel, Dory, et al., "Comparing contact angle measurements and surface tension assessments of solid surfaces", Langmuir 26 (19), (2010), 15289-15294.

Dib-Hajj, Sulayman D, et al., "Human pain in a dish: Native DRG neurons and differentiated pluripotent stem cells". IASP Pain 155, (Sep. 2014), 1681-1682.

Garcia-Parra, Patricia, et al., "Modeling neural differentiation on micropatterned substrates coated with neural matrix components", Frontiers in Cellular Neuroscience, vol. 6, Article 10, (Mar. 14, 2012), 1-12.

Geyer, Florian L, et al., "Superhydrophobic-Superhydrophilic Micropatterning: Towards Genome-on-a-Chip Cell Microarrays", Angewandte Chemie International Edition, vol. 50, Issue 36, (2011), 8424-8427.

Hazeltine, Laurie B, et al., "Engineering the human pluripotent stem cell microenvironment to direct cell fate", NIH Public Access: Author Manuscript, Published in Final Edited Form as Biotechnology Advances, vol. 31, Issue 7, (2013), 38 pgs.

Heller, Daniel A, et al., "Patterned networks of mouse hippocampal neurons on peptide-coated gold surfaces", Biomaterials 26, (2005), 883-889.

Jeong, Gi Seok, et al., "Networked neural spheroid by neuro-bundle mimicking nervous system created by topology effect", Molecular Brain 8:17, BioMed Central, (2015), 12 pgs.

Jing, Gaoshan, et al., "Cell patterning using molecular vapor deposition of self-assembled monolayers and lift-off technique. Acta u Biomaterialia", Acta Biomaterialia 7, (2011), 1094-1103.

Kaisar, Mohammad A, et al., "New experimental models of the blood-brain barrier for CNS drug discovery", Expert Opinion on Drug Discovery, vol. 12, No. 1, (2016), 89-103.

Kim, Deok-Ho, et al., "Guided three-dimensional growth of functional cardiomyocytes on polyethylene glycol nanostructures", Langmuir 22, (2006), 5419-5426.

Kim, Yong Hee, et al., "In vitro extracellular recording and stimulation performance", Journal of Neural Engineering, (Nov. 24, 2015), 10 pgs.

Krinke, Dana, et al., "A microelectrode-based sensor for label-free in vitro detection of ischemic effects on cardiomyocytes", Biosensors and Bioelectronics vol. 24, No. 15, (May 15, 2009), 2798-2803.

Maher, Michael, et al., "A microstructure for interfacing with neurons: the neurochip", Engineering in Medicine and Biology Society,1998. Proceedings of THE20TH Annual International Conference of the IEEE, IEEE—Piscataway, NJ, US, vol. 4, (Oct. 29, 1998), 1698-1702.

Maher, Michael P, et al., "The neurochip: a new multielectrode device for stimulating and recording from cultured neurons", Journal of Neuroscience Methods vol. 87, No. 1, (Feb. 1, 1999), 45-56.

Musick, Katherine, et al., "Three-dimensional micro-electrode array for recording dissociated neuronal cultures", Lab Chip., (Feb. 9, 2010), 18 pgs.

Naik, Pooja, et al., "In Vitro Blood Brain Barrier Models: Current and Perspective Technologies", NIH Public Access: Author Manuscript, Published in Final Edited Form as: Journal of Pharmaceutical Sciences 101(4), (Apr. 2012), 31 pgs.

Nam, Yoonkey, et al., "Gold-Coated Microelectrode Array With Thiol Linked Self-Assembled Monolayers for Engineering Neuronal Cultures", IEEE Transactions on Biomedical Engineering, vol. 51, No. 1, (2004), 158-165.

Panke, Oliver, et al., "A cell-based impedance assay for monitoring transient receptor potential (TRP) ion channel activity", Biosensors and Bioelectronics vol. 26 No. 5, (Jan. 15, 2011), 2376-2382.

Paradis, Alexandre, et al., "Optimization of an nvitro human blood brain barrier model", Methods X 3, (2016), 25-34.

Salisbury, David, "Blood brain barrier on a chip sheds new light on silent killer", News.Vanderbilt EDU, [Online] Retrieved from the internet: <https://news.vanderbilt.edu/2016/12/06/blood-brain-barrier-on-a-chip-sheds-new-light-on-silent-killer/>, (Dec. 6, 2016), 6 pgs.

Stanness, Kathie A, et al., "Morphological and functional characterization of an in vitro blood-brain barrier model", Brain Research 771, (1997), 329-342.

Ueda, Yusuke, et al., "Substrates for human pluripotent stem cell cultures in conditioned medium of mesenchymal stem cells", Journal of Biomaterials Science 23, (2012), 153-165.

Walsh, Frank, et al., "Artificial backbone neuronal network for nano scale sensors", IEEE Conference on Computer Communications Workshop. Shanghai, (2011), 449-454.

Wang, Jack D, et al., "Organization of Endothelial Cells, Pericytes, and Astrocytes into 3D Microfluidic in Vitro Model of the Blood-Brain Barrier", Molecular Pharmaceutics 13, (2016), 895-906.

Yuan, Yuehua, et al., "Chapter 1: Contact Angle and Wetting Properties", Surface Science Techniques, Springer-Verlag Berlin Heidelberg, (2013), 3-34.

"U.S. Appl. No. 15/374,961, Respose filed Sep. 13, 2019 to Communication Pursuant to Article 94(3) EPC dated Nov. 20, 2018", 7 pgs.

"European Application Serial No. 15762878.5, Response Filed Sep. 13, 2019 to Communication Pursuant to Article 94(3) EPC dated Nov. 20, 2018", 7 pgs.

"U.S. Appl. No. 15/374,961, Advisory Action dated Sep. 30, 2019", 6 pgs.

"European Application Serial No. 15762878.5, Communication Pursuant to Article 94(3) EPC dated Feb. 6, 2020" 5 pgs.

"Japanese Application Serial No. 2018-519441, Notification of Reasons for Refusal dated Jan. 7, 2020" W/ English Translation, 8 pgs.

(56) References Cited

OTHER PUBLICATIONS

Kong, et al., "Automatic Liquid Handling for Life Science : A Critical Review of the Current State of the Art", Journal of Laboratory Automation, vol. 17, No. 3, XP055663187, (Feeb. 6, 2012), 18 pages.

* cited by examiner

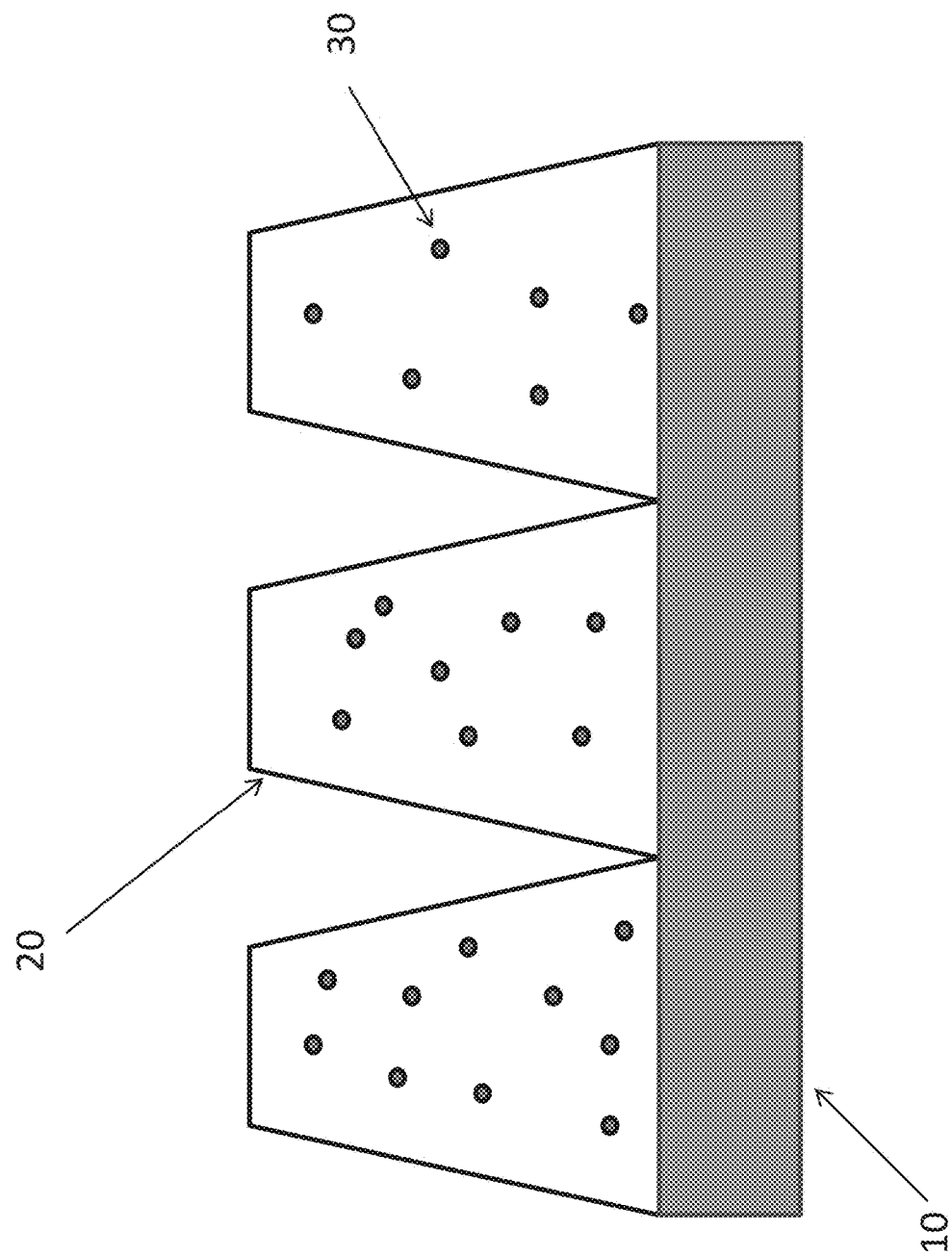

METHOD OF FABRICATING CELL ARRAYS AND USES THEREOF

CROSS-REFERENCE TO RELATED APPLICATIONS

The present application claims the benefit of U.S. application Ser. No. 62/070,508, filed on Aug. 28, 2014, the disclosure of which is incorporated by reference herein.

BACKGROUND

Induced pluripotent stem cells iPSCs are adult cells that have been genetically reprogrammed to an embryonic stem cell-like state by being forced to express genes and factors important for maintaining the defining properties of embryonic stem cells. Although these cells meet the defining criteria for pluripotent stem cells, it is not known if iPSCs and embryonic stem cells differ in clinically significant ways. Mouse iPSCs were first reported in 2006, and human iPSCs were first reported in late 2007. Mouse iPSCs demonstrate important characteristics of pluripotent stem cells, including expressing stem cell markers, forming tumors containing cells from all three germ layers, and being able to contribute to many different tissues when injected into mouse embryos at a very early stage in development. Human iPSCs also express stem cell markers and are capable of generating cells characteristic of all three germ layers.

Although additional research is needed, iPSCs are already useful tools for drug development and modeling of diseases, and scientists hope to use them in transplantation medicine. In the original protocol, viruses were used to introduce the reprogramming factors into adult cells. In animal studies, the virus used to introduce the stem cell factors sometimes causes cancers. Researchers have now developed non-viral delivery strategies that are believed to have less chance of causing cancers.

This breakthrough discovery of iPSCs has created a powerful new way to "de-differentiate" cells whose developmental fates had been previously assumed to be determined. In addition, tissues derived from iPSCs will be a nearly identical match to the cell donor and thus probably avoid rejection by the immune system. The iPSCs strategy creates pluripotent stem cells that, together with studies of other types of pluripotent stem cells, will help researchers learn how to reprogram cells to repair damaged tissues in the human body.

However, creating viable large arrays of iPSCs for high throughput drug screening is problematic due to their sensitivity to environmental factors, available nutrients, fabrication techniques, handling, contamination, and dehydration, as well as the cells immediate three dimensional macro structure environment and the precision equipment necessary to dispense nano liter quantities of molecules of interest to specific array locations.

SUMMARY

The present disclosure provides a fabrication process that results in creating large arrays of living cells, e.g., stem cells, which are subsequently exposed to nanoliter quantities of compounds to test the efficacy on cellular metabolism. In one example, induced pluripotent stem cells iPS are mixed with a ultra violet curable hydrogel matrix, coated onto a support or substrate, then mated to an embossing master tool with a pre-defined micro geometric pattern in a N×N matrix array where N can range from 1 to 10,000, exposed to UV radiation to harden the gel, the embossing tool removed, and the patterned gel, cell, support structure then transferred to an incubation chamber to enhance cellular growth and viability. The N×N matrix of living cells is subsequently exposed to a drug compound delivery system that can address any N in the N×N matrix and dispense nano liter quantities of drug compounds to the site of interest.

In one embodiment, the present disclosure provides for the use of a micro embossing fabrication technology in combination with a nano liter dispensing system that can address individual locations within a cellular array, e.g., an iPSCs matrix array, to deliver drug candidates of interest, thereby providing large matrix arrays for high throughput drug screening.

In one embodiment, this disclosure provides a method of fabricating arrays by the use of micro embossing an ultraviolet curing gel that contains dispersed cells such as stem cells or iPSCs.

In one embodiment, this disclosure provides a method of fabricating cell s arrays by the use of micro embossing where distinct three dimensional micro structures are created that contain dispersed cells.

In one embodiment, this disclosure provides a method of fabricating cell arrays by the use of micro embossing where an array matrix is formed in an N×N pattern where N can range from 1 to 10,000.

In one embodiment, this disclosure provides for exposing arrays, such as those formed either on a film or microwell plate, as to a high precision nano liter dispensing system. In one embodiment, this disclosure provides for exposing arrays to a high precision nano liter dispensing system that can address individual location sites on a N×N iPSCs array.

BRIEF DESCRIPTION OF THE DRAWING

FIG. 1 shows a cross sectional view of one embodiment of the present invention that shows iPSCs dispersed into a hardened gel linear matrix.

DETAILED DESCRIPTION

In one embodiment, FIG. 1 shows a cross sectional view of one example of the present invention that uses iPSC cardiomyocyte cells 30 that have been dispersed and cured into an ultraviolet sensitive hydrogel 20, that was deposited onto a support 10. The support 10 can be comprised of a number of materials such as metal, glass, ceramic, polymer sheet or film and optionally may be a rigid support. The thickness of the support can range from about 12 microns to about 10 millimeters and in one embodiment, about 0.2 to about 1 millimeters. In most cases, the substrate is transparent to allow visual inspection of the contents of the fabricated array on the surface or to allow UV radiation to pass through the material in order to cure the hydrogel-cell mixture onto the surface. In one embodiment, a polymer substrate such as heat stabilized polyester film, polycarbonate, or 1 mm glass is employed. In addition, it may be desirable to have the substrate be porous in order to allow water and nutrients to diffuse into the bottom of the micro embossed 20 hydrogel array. Some porous materials that may be employed are Vycor glass made by Corning, open cell foam film and sheet, or micro porous polymer films that are readily available from multiple suppliers.

In one embodiment, a hydrogel 20, such as one having methacrylate, e.g., gelatin methacrylate, that has iPSCs dispersed into the volume of the gel is coated onto the support 10 and then the gel is cured into the desired geometric shape. In the example of FIG. 1, that shape is a linear array with dimensions of approximately 1.5 mm×1.5 mm×0.25 mm. The linear array shape can be fabricated by mask less direct write photolithography or by using a micro embossing template into which the inverse pattern has been created by diamond engraving, laser ablation, or photolithography, that is pressed into the gel and the gel cured with UV light through a transparent micro embossing template such as silicone or glass or a transparent polymer or glass support 10. A N×N array can be formed onto the support where the number of discrete geometric shapes can range from 2 to over millions. N can have an integer value from 1 to 10,000 but for practical purposes an N×N where N=50 is sufficient and practical. In the present example a 1×16 linear array was fabricated.

In addition to the aforementioned method one skilled in the art can also take a pre-embossed film that has microstructures fabricated as in FIG. 1 then optionally depositing onto the surface an adhesion promoter such as fibronectin, gelatin, hyaluronic acid, carrageen, cellulose, polylysine, polyvinylprylidone, collagen, polyvinylalcohol, or polyethylene oxide or combinations of the aforementioned molecules including polymers thereof. Differentiated iPSCs can then be deposited onto the pre-embossed film and laminated to a N×N where N can range from 1 to 10,000, microplate to form an array.

After the iPSCs array is fabricated, the device is then placed in an incubation chamber at 37° C. with a 5% carbon dioxide gas atmosphere. A number of additives, such as RB+ and Rock inhibitor, that are well known in the art is/are added to a nutrient solution to nourish and prevent the cells from premature death. The cells may be incubated and nourished for up to 3 days or more prior to exposing them to a drug dosing procedure.

In one example, a Labcyte Echo Model 555 nano liter sonic dispensing system was used to deliver 2 heart drugs, Satolol an Antiarrhythmic drug and Isoproteronol a nitric oxide generating compound, to the fabricated array. The drugs were diluted to 2.25 uM in cell media nutrient solution to prevent dehydration. The Echo 555 liquid handler revolutionizes liquid handling with acoustic energy. Sound waves eject precisely sized droplets from a source onto a microplate, slide or other surface suspended above the source. This product does not use tips, pin tools or nozzles completely eliminating contact between the instrument and the liquid. Fluids are transferred in nanoliter increments. Larger volumes are transferred at the rate of hundreds of droplets per second. By using this non contact method it minimizes any contact that could damage or kill the cells as found in other dispensing methods. It also allows for the use of very small quantities thus allowing users to screen molecules that are scarce or difficult to manufacture thus reducing cost. In addition, the X and Y position of the dispensing head can be precisely located over the N×N array location of interest thereby allowing different locations to have a drug of interest administered.

The invention will be described by the following non-limiting example.

EXAMPLE 1

Induced pluripotent stem cells: beating H9 embryonic stem cell derived cardiomyocytes were used on day 25 of differentiation. After disassociation a vial with 1 mL of suspension was produced. The concentration of the suspension was $1.38 \times 10^6$ mL total cells. Within those it was determined that $8.38 \times 10^5$ live cells were present with tryptan blue. The food solution provided was a 50 mL aliquot of RB+ medium (RPMI supplemented with B27 with insulin) for the cells after gel encapsulation. A single drop of Rock inhibitor was added to the nutrient solution. This drug is used to avoid cell death until the cells sense that they are attached to a substrate. The vial was used at a 10 mM concentration. The cells were centrifuged and mixed with GelMa a UV curable matrix and kept at 37° C. The GelMa cell mixture was them placed on a glass support and the area defined by hydrophobic tape. Then a TI DLP mirror chip was used in combination with UV light with a peak frequency of 370 nm to direct write a 1×16 linear array that was approximately 1.5 mm×1.5 mm by 0.25 mm high which takes about 10 seconds. The uncured GelMa was washed away. The support and array was placed in a petri dish and filled with nutrient solution and placed in an incubator at 37° C. in a 5% $CO_2$ atmosphere. Each day the nutrient solution is replaced with fresh media for up to 3 days. After 3 days the arrays were demonstrating a strong beating action and were ready for drug dosing. The array was placed in a Labcyte 555 sonic dispensing machine and the drug molecules precisely dispensed onto the beating cells. During this process the cells were observed with a Lumenera Camera with infinity capture software to visualize the beating cells during the drug dosing.

During the dosing with 10 nM of Satolol an increase in the heart cells beating by 30-40% was observed. During the dosing with Isoproteronol it was observed that the drug removed the refectory period (pause in beating) of some irregularly beating heart cells.

The invention herein is described by example and one particular way of practicing the invention has been described. However the invention as claimed herein is not limited to that specific embodiment are not limited to use therewith and may be used separately or in conjunction with other embodiments disclosed herein. For example, instead of using visual cameras to observe drug effects one can use electronic, magnetic, fluorescence, or fiber optic methods to examine cellular response to drug dosing. Equivalence to the description as hereinafter claimed is considered to be in the scope of protection of this patent. While particular embodiments of the method for fabricating cell micro arrays with subsequent drug dosing has been described it will be appreciated by those skilled in the art that changes and modifications may be made thereto without departing from the invention in its broader aspects as set forth in the following claims.

What is claimed is:
1. A method of fabricating and dosing a viable cell array, comprising:
   providing a mixture of human cells and a UV curable hydrogel matrix, wherein the human cells are embryonic stem cells, induced pluripotent stem cells (iPSC) or cardiomyocytes;
   applying a volume of the mixture to a support, in a specific geometry, to form a N×N array, wherein the substrate comprises a preembossed film substrate having microstructures that provide for the specific geometry, wherein the microstructures are coated with one or more cellular adhesion polymers, and wherein the support is laminated to a microplate;
   exposing the applied volume to UV light to cure each volume in the array and incubating the array under conditions that provide for cell viability;
   contacting each volume of cells in the array with a volume of the one or more compounds using ultrasonic depo- sition, wherein a nanoliter dispensing system provides the volume of the one or more compounds; and detecting whether the one or more compounds affects the viable cells in the array.

2. The method of claim 1 wherein the cells are iPSCs.

3. The method of claim 1 wherein the cells are cardiomyocytes.

4. The method of claim 1 wherein the support is a rigid support.

5. The method of claim 1 wherein the support is a flexible support.

6. The method of claim 1 wherein the support comprises glass, ceramic or a polymer sheet or film.

7. A method of fabricating a stem cell array, comprising:
mixing human induced pluripotent stem cells (iPSC) into a UV curable hydrogel matrix comprising gelatin;
applying the mixture onto a support to provide a N×N array of the hydrogel stem cell mixture, wherein a mold or microstructures in the array provide for a specific geometry; and
applying ITV light to cure the mixture in the presence of a micro mold template.

8. The method of claim 7 further comprising incubating the cells in nutrient solution and optionally exposing the array to one or more compounds.

9. The method of claim 8 wherein the one or more compounds is/are applied via ultrasonic deposition.

10. The method of claim 7 wherein the cells are iPSC derived cardiomyocytes.

11. The method of claim 7 wherein the support is transparent.

12. The method of claim 7 wherein the support is a polyester film, comprises polycarbonate or comprises glass.

13. The method of claim 7 wherein the support is porous.

14. The method of claim 7 wherein the specific geometry is provided by microstructures in the array.

15. The method of claim 14 wherein the microstructures in the array are coated with an adhesion polymer.

16. The method of claim 1 wherein the hydrogel comprises gelatin.

17. The method of claim 16 wherein the hydrogel comprises GelMa.

18. The method of claim 17 wherein the cells are stem cell derived cardiomyocytes.

19. The method of claim 1 wherein the incubation includes contacting the cells in the array with a nutrient solution comprising Rock inhibitor.

* * * * *

UNITED STATES PATENT AND TRADEMARK OFFICE
CERTIFICATE OF CORRECTION

Page 1 of 2

PATENT NO. : 10,625,234 B2
APPLICATION NO. : 14/839170
DATED : April 21, 2020
INVENTOR(S) : Robert John Petcavich It is certified that error appears in the above-identified patent and that said Letters Patent is hereby corrected as shown below:

On the Title Page

On page 2, in Column 1, under "Other Publications", Line 52, delete "2018"," and insert --2019",-- therefor On page 2, in Column 1, under "Other Publications", Line 68, delete "May 31, 2019"," and insert --May 30, 2019",-- therefor On page 2, in Column 2, under "Other Publications", Line 23, delete "Nov. 11," and insert --Nov. 30,-- therefor On page 3, in Column 1, under "Other Publications", Line 2, delete "May 15, 2019"," and insert --May 14, 2019",-- therefor On page 3, in Column 1, under "Other Publications", Line 36, delete "oberlays" and insert --overlays-- therefor On page 3, in Column 1, under "Other Publications", Line 45, delete "Blood?Brain" and insert --Blood-Brain-- therefor On page 3, in Column 2, under "Other Publications", Line 38, delete "nvitro" and insert --in vitro-- therefor On page 3, in Column 2, under "Other Publications", Line 59-61, delete "Respose filed Sep. 13, 2019 to Communication Pursuant to Article 94(3) EPC dated Nov. 20, 2018", 7 pgs." and insert --Response filed Sep. 12, 2019 to Final Office Action mailed Jun. 13, 2019", 7 pgs-- therefor Signed and Sealed this
Twentieth Day of October, 2020

Andrei Iancu
*Director of the United States Patent and Trademark Office*

CERTIFICATE OF CORRECTION (continued)
U.S. Pat. No. 10,625,234 B2

In the Claims

In Column 5, Line 21, in Claim 7, delete "ITV" and insert --UV-- therefor

In Column 6, Line 18, in Claim 18, delete "stern" and insert --stem-- therefor